United States Patent [19]
Slocum

[11] Patent Number: 5,870,832
[45] Date of Patent: Feb. 16, 1999

[54] FRAME FOR GRAVITY-RELATED MEASUREMENT DEVICE

[76] Inventor: Barclay Slocum, 241 Spy Glass Dr., Eugene, Oreg. 97401

[21] Appl. No.: 617,972

[22] Filed: Mar. 18, 1996

[51] Int. Cl.[6] .................................................. G01C 9/00
[52] U.S. Cl. ................................ 33/511; 33/396; 33/572; 33/534
[58] Field of Search .......................... 33/370, 371, 374, 33/375, 376, 511, 512, 572, 534, 1 N

[56] References Cited

U.S. PATENT DOCUMENTS

| | | | |
|---|---|---|---|
| 1,128,881 | 2/1915 | Jones | 33/376 |
| 2,234,436 | 3/1941 | King | 33/374 |
| 2,635,351 | 4/1953 | Marcinkowski | 33/376 |
| 3,229,372 | 1/1966 | Quashnock et al. | 33/512 |
| 3,263,078 | 7/1966 | Thackara et al. . | |
| 3,358,373 | 12/1967 | Martin | 33/512 |
| 3,394,459 | 7/1968 | Grant | 33/534 |
| 3,566,112 | 2/1971 | Luechs . | |
| 3,600,575 | 8/1971 | Chan . | |
| 3,628,761 | 12/1971 | Thomas . | |
| 3,672,607 | 6/1972 | Stauff et al. . | |
| 3,723,006 | 3/1973 | Thomas . | |
| 3,947,970 | 4/1976 | Lesure | 33/375 |
| 4,183,482 | 1/1980 | Jozwiak . | |
| 4,323,049 | 4/1982 | Sogn . | |
| 4,395,829 | 8/1983 | Loftus | 33/374 |
| 4,631,832 | 12/1986 | Schrammen et al. . | |
| 4,651,832 | 3/1987 | Kubo . | |
| 4,658,411 | 4/1987 | Argoud et al. . | |
| 4,872,268 | 10/1989 | Perrault | 33/512 |
| 5,163,228 | 11/1992 | Edwards et al. | 33/512 |
| 5,263,492 | 11/1993 | Voyce . | |
| 5,268,953 | 12/1993 | Van Vlijmen . | |
| 5,387,331 | 2/1995 | Ahern et al. . | |
| 5,481,111 | 1/1996 | Rosar et al. . | |

*Primary Examiner*—Christopher M. Fulton
*Attorney, Agent, or Firm*—Kolisch, Hartwell, Dickinson, McCormack & Heuser

[57] ABSTRACT

A device for positioning an elongate gravity-actuated measuring instrument, such as a goniometer, adjacent two three-dimensional objects to measure an angle between the two objects includes first and second members. The first member is joined to, and extends away from, such instrument, and positionable against a surface of one of such objects. The second member is joined to, and extends away from, such instrument, is spaced from the first member a preselected distance, and is positionable against a surface of the other of such objects. Preferably, the first member is formed as a frame that is coupled to such instrument, and the second member is formed as an elongate positioning probe that is coupled to the frame. The device may also be formed with rotational-attachment structure, both to allow attachment of the second end of the probe to the frame and, when attached, to allow rotation of the probe about an axis defined by the long axis of the probe. In addition, the device may be formed with probe-positioning structure that allows a user to place the probe in a preselected number of positions for ultimate desired placement against such surface of the other of such objects.

2 Claims, 1 Drawing Sheet

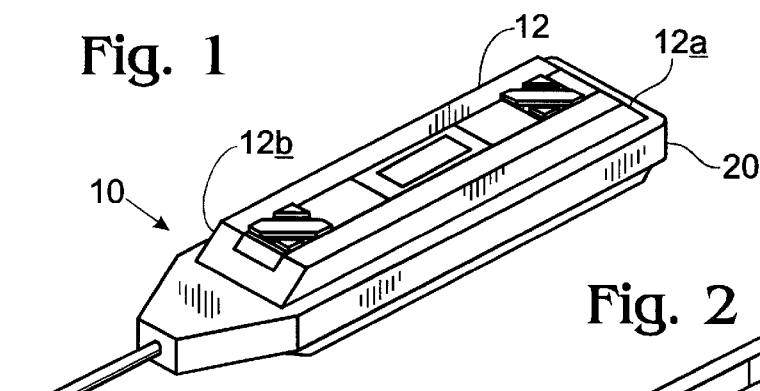
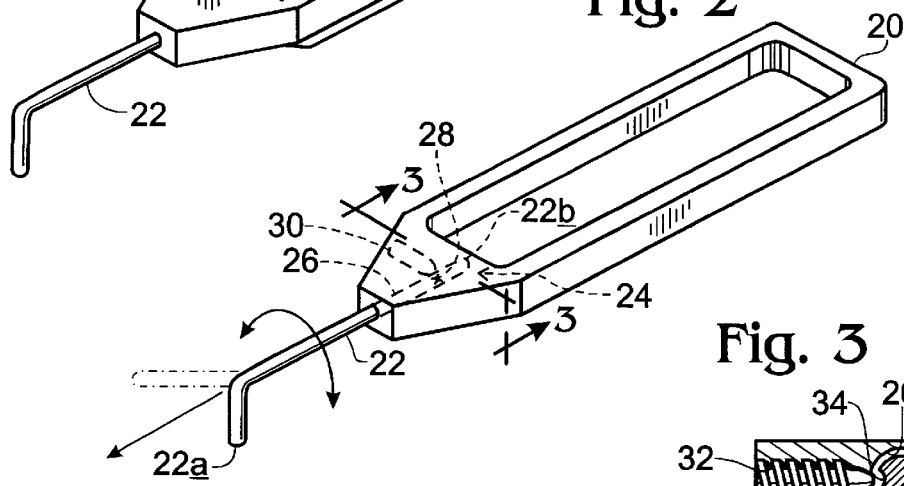
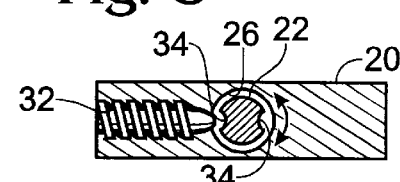
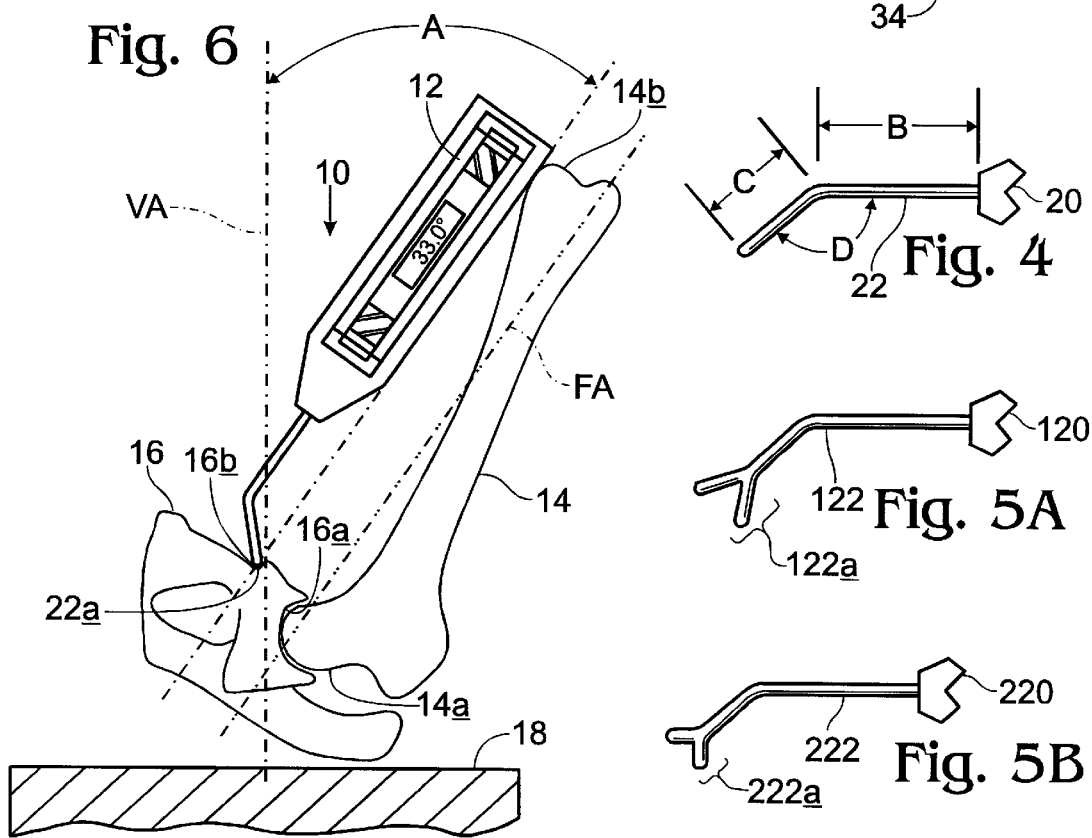
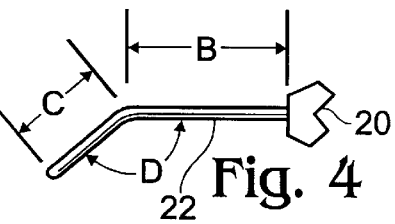
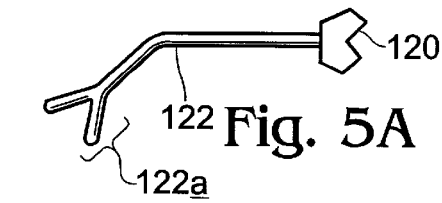
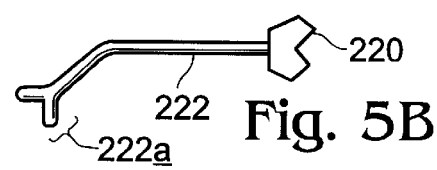

FRAME FOR GRAVITY-RELATED MEASUREMENT DEVICE

BACKGROUND AND SUMMARY OF THE INVENTION

The present invention relates generally to gravity-actuated measuring devices and instruments such as goniometers and, more particularly, to a novel frame for such instruments and method for using the same.

Gravity-actuated measuring devices such as levels and goniometers are known. When using a goniometer to measure an angle between two objects, it is often difficult to place the goniometer in such a way to ensure an accurate measurement. Such difficulty may arise for several reasons.

First, the objects may be covered by other items or otherwise obstructed so that the goniometer cannot easily be placed in the desired position to make the desired measurement. Second, the user may not have the ability to hold the goniometer in the desired position in a sufficiently steady manner to produce an accurate measurement. Such inability on the part of the user may be due to a physical disability, but could also be caused by the desired position for the goniometer. That is, the user may have to assume a difficult position to place the goniometer in the desired position so that even without a physical disability, the user cannot hold the goniometer in a sufficiently steady manner.

One representative application for goniometers that presents the above problems is in orthopedic surgery, and particularly veterinary orthopedic surgery. In that context, the surgeon will place the goniometer in a desired position to measure an angle between two bone regions. The two bone regions may each be separate bones, or may be part of the same bone.

In veterinary orthopedic surgery, bone regions are often obstructed by musculature that makes it difficult to place the goniometer in the desired position. In addition, the surgeon will often have to place their own body and hands in a difficult position to place the goniometer in the desired position. The result is that it is difficult for the surgeon to hold the goniometer in a sufficiently steady manner, ultimately to achieve the desired angular measurement.

Conventional gravity-actuated measuring instruments such as goniometers do not provide solutions to the above problems.

Accordingly, it is a principal object of the present invention to provide a system for positioning a gravity-actuated measuring instrument such as a goniometer.

Another object is to provide such a system that allows positioning of such instrument in a sufficiently steady manner to allow accurate measurement of an angle between two objects.

Yet another object is to provide such a system that provides an enclosure for such instrument to protect it during use.

Another important object of the invention is to provide such a system that includes a placement mechanism that accommodates placement of the instrument in the desired position when that position is obstructed by other material.

Yet another object is to provide a method of using such a system.

It is also an object of the invention to provide such a system that can be cost-effectively manufactured.

In brief summary, one aspect of the invention includes a device for positioning an elongate gravity-actuated measuring instrument, such as a goniometer, adjacent two three-dimensional objects to measure an angle between the two objects includes first and second members. The first member is joined to, and extends away from, such instrument, and positionable against a surface of one of such objects. The second member is joined to, and extends away from, such instrument, is spaced from the first member a preselected distance, and is positionable against a surface of the other of such objects.

Preferably, the first member is formed as a frame that is coupled to such instrument, and the second member is formed as an elongate positioning probe that is coupled to the frame. The device may also be formed with rotational-attachment structure, both to allow attachment of the second end of the probe to the frame and, when attached, to allow rotation of the probe about an axis defined by the long axis of the probe. In addition, the device may be formed with probe-positioning structure that allows a user to place the probe in a preselected number of positions for ultimate desired placement against such surface of the other of such objects.

Yet another aspect of the invention is to provide a method of positioning a goniometer adjacent two bone regions to measure an angle between the two regions. The method includes the steps of selecting an elongate goniometer-positioning device and coupling the same to such goniometer, and first placing one end of the device against a surface of one of such regions. The method also includes the steps of next placing another end of the device against a surface of the other of such regions, and using the goniometer to measure such an angle between the two regions after performing the first and next placing steps.

These and other objects and advantages of the invention will be more clearly understood from a consideration of the accompanying drawings and the following description of the preferred embodiment.

BRIEF DESCRIPTION OF THE DRAWINGS

FIG. 1 is an isometric view showing the preferred embodiment of the goniometer-positioning device of the present invention, with the device being joined to a goniometer.

FIG. 2 is like FIG. 1 except that the goniometer has been removed.

FIG. 3 is an enlarged, fragmentary view through line 3—3 of FIG. 2 that shows how two elements of the device of the invention are attached.

FIG. 4 is a fragmentary, top view of a probe element of the device of the invention.

FIGS. 5A–B show alternate embodiments of the probe element shown in FIG. 4.

FIG. 6 shows a fragmentary, partially schematic view of the device of the invention in a reduced scale relative to FIG. 1, with the device in use to position a goniometer adjacent a canine femur and pelvis.

DETAILED DESCRIPTION OF THE PREFERRED EMBODIMENTS

FIG. 1 depicts an isometric view of the goniometer-positioning device of the present invention, being made in accordance with its preferred embodiment and indicated at 10. Of course, the device of the invention could be used for any gravity-actuated measuring instrument. The remaining description of the invention will be in the context of orthopedic veterinary surgery, but it should be understood that the invention could be used for any suitable application.

Referring to FIGS. 1–2 and 6, device 10 is for positioning an elongate gravity-actuated measuring instrument, such as goniometer 12 adjacent two three-dimensional objects, such as canine femur 14 and canine pelvis 16, to measure an angle between the two bones. The canine bones are shown in FIG. 6 in a somewhat schematic form, i.e. the remainder of the dog, such as surrounding musculature, is not depicted.

Still referring to FIG. 6, and for perspective so the reader can understand how goniometer 12 will function, a surgery table 18 is shown with the canine bones positioned on the table as they would be when an orthopedic veterinary surgeon is performing surgery. Femur 14 is shown with a femoral neck 14a placed within acetabulum 16a of pelvis 16. An angle A is defined by a vertical axis VA running through pelvis 16 and shown by dot-dash lines, and an approximate force axis FA of femur 14 running generally parallel to the long axis of femur 14 and shown by double-dot-dash lines. As will be described, goniometer 12 will be used with device 10 to measure angle A at 33° as shown on the display of goniometer 12 in FIG. 6. A suitable electronic goniometer with such a display is commercially available from a U.S. company known as Wedge Innovations.

As a last preliminary comment before describing further the elements of device 10, and continuing focus on FIG. 6, it should be understood that canine musculature such as the medial thigh muscles (undepicted) make it difficult to place goniometer 12 in the position shown in FIG. 6.

Now, referring back to FIGS. 1–4, device 10 includes a first member 20 joined to, and extending away from, goniometer 12, and being positionable against a surface 14b of femur 14 (see FIG. 6). A second member 22 also is joined to, and extends away from, goniometer 12, and second member 22 is spaced from first member 20 a preselected distance. Second member 22 is also positionable against a surface 16b of pelvis 16 (see again FIG. 6). More specifically, surface 16b is caudal to the canine iliopectineal imminence. The preselected distance is to provide at least two points of contact with the desired bones wherein the points are separated sufficiently to allow the goniometer to be held steady. There are numerous, suitable preselected distances, and in the preferred application, a distance in the range of about 6–12 inches has been found suitable.

Preferably, first member 20 is formed as a frame for goniometer 12, and frame 20 is joined to a first end 12a of goniometer 12. Second member 22 is preferably formed as an elongate, cylindrical, positioning probe and is joined to a second end 12b of goniometer 12. Probe 22 is joined to goniometer 12 via attachment or coupling to frame 20 as will be described.

Referring to FIG. 2, probe 22 has a long axis shown by the straight arrow, is angular and includes opposing first and second ends 22a–b. The angular shape accommodates desired placement of first end 22a against surface 16b (see FIG. 6).

Referring to FIGS. 2–3, frame 20 is formed with rotational-attachment structure 24, both to allow attachment of second end 22b of probe 22 to frame 20 and, when attached, to allow rotation of probe 22 (see curved arrows in FIG. 2) about an axis defined by the long axis of the probe (again, see straight arrow in FIG. 2). Rotational-attachment structure 24 is preferably formed by (1) a primary recess 26 in frame 20 that receives second end 22b of probe 22, (2) a circumferential groove 28 that is formed in probe 22 near second end 22b, (3) a secondary threaded recess 30 in frame 20 that communicates with primary recess 26, and (4) a set screw 32 (see FIG. 3) drivable through secondary recess 30 and extendable a preselected distance of about 1/16- to 1/8-inch into primary recess 26 (see FIG. 3). Set screw 32 is operable to hold second end 22b in primary recess 26 and to allow probe 22 to rotate. Groove 28 provides a bearing surface during rotation of probe 22 for the operative end of set screw 32 shown in FIG. 3.

Still referring to FIGS. 2–3, probe-positioning structure 34 is formed preferably in probe 22 to allows a veterinary surgeon using device 10 to place the probe in a preselected number of positions for ultimate desired placement against a bone surface. Probe-positioning structure 34 is preferably formed as opposing depressions formed in opposing sides of probe 22. Depressions 34 act as detents to hold probe 22 in either of the two positions shown in FIG. 2, i.e. the one shown in solid lines and the one shown in dashed lines. The capability of rotating probe 22 to at least two positions has been found helpful to accommodate desired placement of the probe among the various obstructions presented by musculature and other tissue.

Referring to FIG. 4, the dimensions of probe 22 are preferably as follows: linear section B is from about 1–4" long, angled section C is from about 1–2" long, and angle D is about 40–60°. The shape of probe 22 allows placement around obstructive material, such as medial thigh muscles (undepicted) in the veterinary surgery application shown in FIG. 6.

Referring to FIGS. 5A–B, alternate embodiments of probe 22 are shown as probe 122 and 222, respectively. Probe 122 includes a first end 122a that has a Y-shape, and probe 222 includes a first end 222a that has a cupped shape. The idea behind the alternate embodiments is to provide a stabilizing feature to the first end of the probe to maintain even better, further stable contact with a desired surface such as a bone region.

With respect to material choices for device 10 and its elements, any suitable material can be used such as metal, plastic or composite.

OPERATION AND PREFERRED METHOD OF PRACTICING THE INVENTION

In use, the surgeon selects device 10, couples it to goniometer 12, and first places one end of the device (such as frame 20) against a surface of femur 14 (such as 14b). The surgeon next places another end of the device (such as probe 22) against a surface of pelvis 16 (such as surface 16b near the iliopectineal imminence). Finally, the surgeon uses goniometer 12 to measure an angle between femur 14 and a vertical axis as shown in FIG. 6 and described above.

The invention therefore achieves its objects by providing a device 10 that provides a system for positioning a goniometer. Device 10 also allows positioning of the goniometer in a sufficiently steady manner to allow accurate measurement of an angle between two objects. Frame 20 of device 10 also provides an enclosure for the goniometer to protect it during use. The shape of probe 22, and the rotational attachment of probe 22 to frame 20, provide a placement mechanism that accommodates placement of the goniometer in a desired position when that position is obstructed by other material such as canine musculature. Device 10 can also be cost-effectively manufactured.

Accordingly, while a preferred embodiment of the invention has been described herein, it is appreciated that modifications are possible that are within the scope of the invention.

It is claimed and desired to secure by letters patent:
1. A gravity-actuated measuring instrument system capable of positioning the instrument adjacent first and second three-dimensional objects to measure an angle between the two objects, comprising:

a gravity-actuated measuring instrument;

a frame joined to, and partially enclosing, the instrument, the frame including plural sides, and being positionable against a surface of the first object;

an elongate, cylindrically shaped probe member joined to, and extending a preselected distance away from the frame, the probe member being positionable against a surface of the second object, and the probe member having first and second ends, wherein the second end is joined to the frame, and the first end is positionable against such surface of the second object, and wherein the probe member is formed with an angular shape to accommodate desired positioning relative to the second object, wherein the frame is also formed with rotational-attachment structure, both to allow attachment of the second end of the probe member to the frame and, when attached, to allow rotation of the probe member about an axis defined by a long axis of the probe member, and wherein the probe member is movable between first and second orientations relative to the frame, and wherein each first and second orientation results in a preselected one of the sides of the frame to be positioned against the first object; and wherein the rotational-attachment structure is formed by a primary recess in the frame that receives the second end of the probe member, a circumferential groove that is formed in and near the second end of the probe member, a secondary threaded recess in the frame that communicates with the primary recess, and a set screw drivable therethrough and extendable a preselected distance into the primary recess, the set screw being operable to hold the second end in the primary recess and to allow the probe member to rotate, with the groove providing a bearing surface for the set screw during rotation of the probe member.

2. A goniometer system capable of positioning a goniometer adjacent first and second animal anatomical elements to measure an angle between the two elements, comprising:

a goniometer;

a frame joined to, and partially enclosing the goniometer, the frame including plural sides, and being positionable against a surface of the first element;

an elongate, cylindrically shaped probe member joined to, and extending a preselected distance away from, the frame, the probe member being positionable against a surface of the second element, and the probe member having first and second ends, and wherein the second end is joined to the frame, and the first end is positionable against such surface of the second object, and wherein the probe member is formed with an angular shape to accommodate desired positioning relative to the second object wherein the frame is formed with rotational-attachment structure, both to allow attachment of the second end of the probe member to the frame and, when attached, to allow rotation of the probe member about an axis defined by the long axis of the probe member and wherein the probe member is movable between first and second orientations relative to the frame, and wherein each fast and second orientation results in a preselected one of the sides of the frame to be positioned against the first object; and wherein the rotational-attachment structure is formed by a primary recess in the frame that receives the second end of the probe member a circumferential groove that is formed in and near the second end of the probe member, a secondary threaded recess in the frame that communicates with the primary recess and a set screw drivable therethrough and extendable a preselected distance into the primary recess, the set screw being operable to hold the second end in the primary recess and to allow the probe member to rotate, with the groove providing a bearing surface for the set screw during rotation of the probe member.

* * * * *